US008614248B2

(12) United States Patent
Burstein et al.

(10) Patent No.: US 8,614,248 B2
(45) Date of Patent: Dec. 24, 2013

(54) USE OF ESTERS OF LONG-CHAIN FATTY ACIDS FOR TREATMENT OF AUTOIMMUNE DISEASES

(75) Inventors: Pinchas Burstein, Ramat Hasharon (IL); Avraham Ben-Nun, Yavne (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 2505 days.

(21) Appl. No.: 10/474,696

(22) PCT Filed: Apr. 11, 2002

(86) PCT No.: PCT/IL02/00296
§ 371 (c)(1),
(2), (4) Date: Apr. 12, 2004

(87) PCT Pub. No.: WO02/083059
PCT Pub. Date: Oct. 24, 2002

(65) Prior Publication Data
US 2004/0186072 A1 Sep. 23, 2004

(30) Foreign Application Priority Data

Apr. 11, 2001 (IL) .......................... 142537

(51) Int. Cl.
*A01N 43/04* (2006.01)
*A01N 43/00* (2006.01)
*A61K 31/70* (2006.01)
*A61K 31/33* (2006.01)

(52) U.S. Cl.
USPC ....................................... 514/549

(58) Field of Classification Search
None
See application file for complete search history.

(56) References Cited

U.S. PATENT DOCUMENTS

| 5,231,087 A | 7/1993 | Thornfeldt |
| 5,683,698 A * | 11/1997 | Chavali et al. ............... 424/756 |
| 5,792,774 A | 8/1998 | Haughan et al. |
| 2001/0033838 A1* | 10/2001 | Farmer ......................... 424/115 |

FOREIGN PATENT DOCUMENTS

| EP | 0 0120 169 A | 10/1984 |
| WO | WO 01/03688 A | 1/2001 |

OTHER PUBLICATIONS

Lastra, et al. "Mediterranean Diet and Health: Biological Importance of Olive Oil." Current Pharmaceutical Design, 2001, 7, 933-950.*
Yaqoob. Monounsaturated fats and immune function. Brazilian Journal of Medical and Biological Research (1998), 31: 453-465.*
Calder. The effects of fatty acids on lymphocyte functions. Brazilian J Med Biol. Res, 1993, 26: 901-917.*
Raines (Handbook of Clinical Neurology, 3(47): 429-466, 1985).*
t'Hart et al. Drug Discovery Today, 2004, 9, 517-524.*
Swanborg et al. Clinical Immunology and Pathology, 77: 4-13, 1995.*
Dijikstra et al. TIPS Reviews, 14: 124-129, 1993.*
Alvord et al. (Annals Neurology, 6(6): 461-468, 1978).*
Yoon (Science, 259: 1263, 1993).*
Weiner et al. Science, 259, 5099, pp. 1321, Feb. 26, 1993.*
Van Noort et al. International Review of Cytology, 178: 127-205, 1998.*
Merriam-Webster Dictionary online. Definition of organ. 2009. http://www.merriam-webster.com/dictionary/organ.*
http://www.thefreedictionary.com/joint.*
Liblau et al. Th1 and Th2 CD4+ T cells in the pathogenesis of organ-specific autoimmune diseases. Immunology Today, vol. 16, No. 1, 1995.*
Dhopeshwarkar et al. Role of oleic acid in the metabolism of essential fatty acids. Journal of American Oil Chemists' Society, vol. 38, No. 6, 1961, 297-301.*
Patent abstracts of Japan vol. 1995, No. 03, (Apr. 28, 1995) & JP 6 345644 A (Unitika Ltd), Dec. 20, 1994.
Database WPI Section Ch, Week 199429 Derwent Publications Ltd., London, GB; AN 1994-238645 XP002312341 & JP 06 172168 A (Tsuji K) Jun. 21, 1994.
Lassmann H. "Chronic relapsing experimental allergic encephalomyelitis: its value as an experimental model for multiple sclerosis" Journal of neurology: 229(4) pp. 207-220 (1983).
Lublin F.D. "Relapsing experimental allergic encephalomyelitis. An autoimmune model of multiple sclerosis" Springer seminars in immunopathologyl: 8(3) pp. 197-208 (1985).
Ben-Nun A., Yossefi S. "Reversal of autoimmune encephalomyelitis by membranes presenting myelin basic protein-associated class II MHC molecule as an approach to immunotherapy of organ-specific autoimmune diseases" European Journal of Immunology: 20(2) pp. 357-361 (1990).
Beraud-Juven E. "Multiple sclerosis and experimental autoimmune encephalomyelitis" La Revue du praticient: 44 (1) pp. 69-74 (1994).

(Continued)

*Primary Examiner* — Anna Pagonakis
(74) *Attorney, Agent, or Firm* — Browdy and Neimark, PLLC

(57) ABSTRACT

Agents selected from: (i) a $C_1$-$C_{24}$ alkyl ester of a saturated or cis-unsaturated $C_{10}$-$C_{24}$ fatty acid; (ii) a monoester or polyester of a polyol having at least four hydroxy groups with a saturated or cis-unsaturated $C_{10}$-$C_{24}$ fatty acid or an anhydro derivative thereof; (iii) a monoester or polyester of a mono-, di- or poly-saccharide with a saturated or cis-unsaturated $C_{10}$-$C_{24}$ fatty acid; (iv) an amide of a saturated or cis-unsaturated $C_{10}$-$C_{24}$ fatty acid with an aliphatic or aromatic amine or with an amino acid, peptide, protein or aminosaccharide; and (v) combinations of any of (i) to (iv), can be used for treatment of autoimmune diseases and other immune-associated inflammatory disorders. Preferred agents are ethyl oleate and mannide monooleate or a combination thereof.

6 Claims, 8 Drawing Sheets

(56) References Cited

OTHER PUBLICATIONS

Owens T., Sriram S.C. "The immunology of multiple sclerosis and its animal model, experimental allergic encephalomyelitis" Neurologics Clinics: 13(1) pp. 51-73 (1995).

Martin R., McFarland H.F. "Immunological aspects of experimental allergic encephalomyelitis and multiple sclerosis" Critical Reviews in Clinical Laboratory Sciences: 32(2) pp. 121-182 (1995).

Eng L.F. et al "Inflammation in EAE: role of chemokine/cytokine expression by resident and infiltrating cells" Neurochemical Research: 21(4) pp. 511-525 (1996).

Karlik S.J. et al. "Correlation between MRI and clinico-pathological manifestations in Lewis rats protected from experimental allergic encephalomyelitis by acylated synthetic peptide of myelin basic protein" Magnetic Resonce Imaging: 17(5) pp. 731-737 (1999).

Cohen I.R., Schwartz M. "Autoimmune maintenance and neuroprotection of the central nervous system" Journal of neuroimmunology: 100(1-2) pp. 111-114 (1999).

Tuohy V.K. et al "Spontaneous regression of primary autoreactivity during chronic progression of experimental autoimmune encephalomyelitis and multiple sclerosis.". The Journal of experimental medicine: 5;189 (7) pp. 1033-1042 (1999).

Fazekes G., Tabira T. "What transgeen and knockout mouse models teach us about experimental autoimmune encephalomyelitis" Reviews in immunogenetics: 2(1) pp. 115-132 (2000).

Mohamed A. et al. "Improvement of experimental allergic encephalomyelitis (EAE) by thymoquinone; an oxidative stress inhibitor" Biomedical sciences instrumentation: 39 pp. 440-445 (2003).

El Behi M. et al "New insights into cell responses involved in experimental autoimmune encephalomyelitis and multiple sclerosis" Immunology letters: 96(1) pp. 11-26 (2005).

Teitelbaum D. et al "Suppression of experimental allergic encephalomyelitis by a synthetic polypeptide" European Journal of Immunology: 1(4) pp. 242-248 (1971).p.

Teitelbaum D. et al "Suppression by several synthetic polypeptides of experimental allergic encephalomyelitis induced in guinea pigs and rabbits with bovine and human basic encephalitogen" European Journal of Immunology: 3 (5) pp. 273-279 (1973).

Teitelbaum D. et al "Suppression of experimental allergic encephalomyelitis in rhesus monkeys by a synthetic basic copolymer" Clinical Immunology and Immunopathology: 3(2) pp. 256-262 (1974).

Keith A.B. et al. "The effect of Cop 1, a synthetic polypeptide, on chronic relapsing experimental allergic encephalomyelitis in guinea pigs" Journal of the neurological sciences: 42(2) pp. 267-274 (1979).

Abramsky O. et al "Effect of a synthetic polypeptide (COP 1) on patients with multiple sclerosis and with acute disseminated encephalomeylitis. Preliminary report" Journal of the neurological sciences: 31(3) pp. 433-438 (1977).

Bornstein M.B. et al "Multiple sclerosis: trial of a synthetic polypeptide" Annals of neurology: 11(3) pp. 317-319 (1982).

Bornstein M.B. et al "A pilot trial of Cop 1 in exacerbating-remitting multiple sclerosis" The New England Journal of Medicine: 317(7) pp. 408-414 (1987).

Teitelbaum D. et al. "Cop 1 as a candidate drug for multiple sclerosis" Journal of neural transmission. Supplementum: 49 pp. 85-91 (1997).

* cited by examiner

USE OF ESTERS OF LONG-CHAIN FATTY ACIDS FOR TREATMENT OF AUTOIMMUNE DISEASES

FIELD OF THE INVENTION

The present invention relates to anti-inflammatory agents and, more particularly, to some esters of long-chain fatty acids useful in the therapy of autoimmune diseases and other immune-associated inflammatory disorders.

ABBREVIATIONS: CFA: complete Freund's adjuvant; EAE: experimental autoimmune encephalomyelitis; EOA: ethyl oleate; IDDM: insulin-dependent diabetes mellitus; IFA: incomplete Freund's adjuvant; MBP: myelin basic protein; MMO: mannide mono-oleate: MS: multiple sclerosis; MSCH: mouse spinal cord homogenate; PBS: phosphate-buffered saline; PLP: proteolipid protein.

BACKGROUND OF THE INVENTION

An autoimmune disease results from the failure of the immune system to maintain self-tolerance to antigen(s) in the affected organ. Over forty systemic and organ-specific autoimmune diseases have been observed, among which some, like systemic lupus erythematosus and myasthenia gravis, are mediated by antibodies, while others, such as multiple sclerosis (MS), insulin-dependent diabetes mellitus, rheumatoid arthritis and thyroiditis, are mediated by T-cells reactive against specific antigens in the relevant target organ. In the target organ, these abnormally activated T-cells initiate an inflammatory reaction whereby other T-cells, B-cells and macrophages as well as other mononuclear cells are recruited, resulting in organ-specific tissue damage.

Human autoimmune diseases can be divided into two broad categories: organ-specific and systemic autoimmune diseases.

Organ-specific autoimmune diseases include MS, insulin-dependent diabetes mellitus (IDDM), rheumatoid arthritis, several forms of anemia (aplastic, hemolytic), autoimmune hepatitis, thyroiditis, iridocyclitis, scleritis, uveitis, orchitis, myasthenia gravis, idiopathic thrombocytopenia purpura, and inflammatory bowel diseases such as Crohn's disease and ulcerative colitis.

Systemic autoimmune diseases include scleroderma and systemic sclerosis, Sjogren's syndrome, undifferentiated connective tissue syndrome, antiphospholipid syndrome, different forms of vasculitis (polyarteritis nodosa, allergic granulomatosis and angiitis, Wegner's granulomatosis, Kawasaki disease, hypersensitivity vasculitis, Henoch-Schoenlein purpura, Behcet's Syndrome, Takayasu arteritis, giant cell arteritis, thromboangitis obliterans), systemic lupus erythematosus, polymyalgia rheumatica, psoriasis vulgaris and psoriatic arthritis, polymyositis and other idiopathic inflammatory myopathies, relapsing panniculitis, relapsing polychondritis, lymphomatoid granulomatosis, erythema nodosum, ankylosing spondylitis, Reiter's syndrome, and different forms of inflammatory dermatitis.

Several animal models have been developed to study autoimmunity. Among the autoimmune diseases, multiple sclerosis (MS) and its animal model, experimental autoimmune encephalomyelitis (EAE), have been thoroughly investigated as a prototypic organ-specific T-cell mediated autoimmune disease. MS is an autoimmune inflammatory disease of the central nervous system (CNS) characterized by primary demyelination, which manifests itself clinically by varying degrees of neurological impairment in different patients. The disease is believed to result from an abnormal T-cell response to myelin antigens in the CNS.

Several myelin proteins have been identified as potential primary target antigens against which the deleterious autoimmune cells are directed, on the basis of their ability to cause EAE in laboratory animals (Kerlero de Rosbo and Ben-Nun, 1998). EAE, the purported experimental model for MS, presents many similarities in neuropathological and clinical manifestations with its human counterpart. EAE can be actively induced in genetically susceptible strains of laboratory animals by immunization with spinal cord homogenate, purified myelin proteins such as myelin basic protein (MBP), proteolipid protein (PLP) and myelin oligodendrocyte glycoprotein (MOG), or peptides thereof, emulsified in an adjuvant or passively induced by injection of activated $CD4^+$ T-cell lines or clones specific for those myelin antigens (Kerlero de Rosbo and Ben-Nun, 1999). EAE induced in SJL/J mice with PLP 139-151 or in C3H.SW mice with MOG 35-55,is a severe chronic disease suitable for immunomodulatory studies (Kerlero de Rosbo and Ben-Nun, 1999).

Numerous immune-specific and non immune-specific approaches to therapy of autoimmune diseases have been investigated in experimental animal models. In the context of MS, some of these approaches have resulted in the development of drugs such as Copaxone and Interferon-$\beta$, the effectiveness of which in treatment of MS is limited.

Immune-specific approaches to therapy of autoimmune diseases have been thoroughly investigated. Among these, the administration of autoantigens has yielded promising results in rodents. Thus, injection and/or oral administration of MBP, MBP peptides, PLP peptides or whole myelin, could suppress the development of EAE in rodents, and oral administration of glutamic acid decarboxylase (GAD), S-antigen or collagen type II was effective in suppressing the development of diabetes, uveitis or rheumatoid arthritis, respectively, in laboratory animals. However, the results of a phase II clinical trial by oral feeding of MS patients with myelin were not encouraging.

One of the major difficulties in devising effective immune-specific therapy to autoimmune diseases is the complexity of the potentially deleterious autoimmune T-cell response whereby a multiplicity of autoantigens can be targeted. Accordingly, non immune-specific treatments via immunosuppressive agents such as corticosteroids, cyclosporin A, azathioprine, methotrexate etc, are often applied in MS, as well as in other autoimmune diseases. However, these treatments are often associated with "generalized immunosuppression" and side effects of varying severity in treated patients.

It would be very desirable to discover new agents that could be used for the therapy of autoimmune diseases and other immune-associated inflammatory disorders.

SUMMARY OF THE INVENTION

It has now been unexpectedly found, according to the present invention, while investigating non antigen-specific immunomodulation of autoimmune diseases via compounds whose effect is not related to generalized immunosuppression, that some esters of long-chain fatty acids represented by ethyl oleate (hereinafter EOA) and mannide mono-oleate (hereinafter MMO), which are known to be non-toxic when injected into humans, are highly effective in protecting against the development of severe chronic EAE. Furthermore, treatment of ongoing disease with either agent or their combination resulted in considerable reduction or abrogation of neurological impairment.

The present invention thus relates to a pharmaceutical composition for the treatment of autoimmune diseases and other immune-associated inflammatory disorders comprising as active ingredient an agent selected from:

(i) a $C_1$-$C_{24}$ alkyl ester of a saturated or cis-unsaturated $C_{10}$-$C_{24}$ fatty acid;
(ii) a monoester or polyester of a polyol having at least four hydroxy groups with a saturated or cis-unsaturated $C_{10}$-$C_{24}$ fatty acid or an anhydro derivative thereof;
(iii) a monoester or polyester of a mono-, di- or polysaccharide with a saturated or cis-unsaturated $C_{10}$-$C_{24}$ fatty acid;
(iv) an amide of a saturated or cis-unsaturated $C_{10}$-$C_{24}$ fatty acid with an aliphatic or aromatic amine or with an amino acid, peptide, protein or aminosaccharide; and
(v) combinations of any of (i) to (iv).

In another embodiment, the invention relates to the use of an agent as defined in (i) to (iv) above or a combination thereof for the preparation of a pharmaceutical composition for the treatment of autoimmune diseases and other immune-associated inflammatory disorders.

In still another embodiment, the invention relates to a method for the treatment of an autoimmune disease or any other immune-associated inflammatory disorder, which comprises administering to an individual in need thereof an agent as defined in (i) to (iv) above or a combination thereof.

BRIEF DESCRIPTION OF THE FIGURES

FIG. 4A—Development of EAE in mice injected i.p. daily with EOA or IFA. SJL/J mice were induced to develop EAE by PLP 139-151/CFA. On day 12 after encephalitogenic challenge, the mice were daily-injected i.p. with 100 μl of either PBS (control; 5 mice), EOA (13 mice) or IFA (14 mice), until day 35 post-encephalitogenic challenge. FIG. 4B—Clinical course of EAE after cessation of treatment in fully recovered mice, subgroups EOA-F (8 mice) and IFA-F (11 mice). FIG. 4C—Clinical course of EAE after treatment was reinstated from day 40 in partially recovered mice, subgroups EOA-P (5 mice) and IFA-P (3 mice).

DETAILED DESCRIPTION OF THE INVENTION

Figure 1:
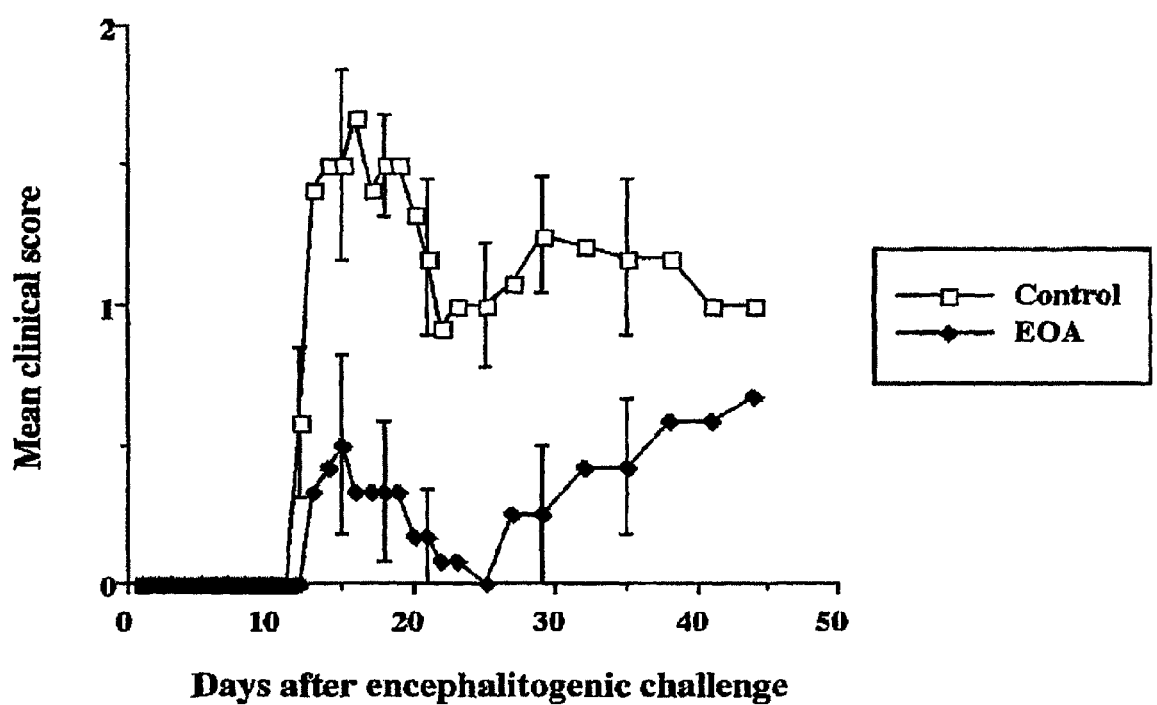
FIG. 1 shows that subcutaneous (s.c.) administration of ethyl oleate (EOA) protects against the development of EAE. SJL/J mice were induced to develop EAE by PLP peptide 139-151 in CFA. 100 μl EOA were injected s.c. daily from the day of encephalitogenic challenge (day 0) until day 11, when first neurological impairment was observed. Subsequently, EOA treatment was continued every alternate day (day 13, 15 and 17), followed by three more injections on days 20, 23 and 26.

The present invention provides esters and amides of long-chain fatty acids as agents for the treatment of autoimmune diseases and other immune-associated inflammatory disorders.

The agent for use according to the invention may be derived from a saturated or cis-unsaturated $C_{10}$-$C_{24}$ aliphatic acid, preferably $C_{16}$-$C_{20}$, most preferably $C_{18}$ fatty acid, such as, but not limited to, a saturated fatty acid selected from capric acid, lauric acid, myristic acid, palmitic acid, stearic acid and arachidic acid, or a cis-unsaturated fatty acid selected from palmitoleic acid (cis-9-hexadecenoic acid), oleic acid (cis-9-octadecenoic acid), cis-vaccenic acid (cis-11-octadecenoic acid), linoleic acid (cis-9,12-octadecadienoic acid), γ-linolenic acid (cis-6,9,12-octadecatrienoic acid), linolenic acid (cis-9,12,15-octadecatrienoic acid) and arachidonic acid (cis-5,8,11,14-eicosatetraenoic acid). In a most preferred embodiment, the fatty acid is oleic acid.

According to one embodiment of the invention, the agent is an alkyl ester of a saturated or cis-unsaturated $C_{10}$-$C_{24}$ aliphatic acid, preferably $C_{16}$-$C_{20}$, most preferably $C_{18}$ fatty acid, such as, but not limited to, a $C_1$-$C_{24}$, preferably $C_1$-$C_8$, most preferably $C_2$ alkyl ester. Thus the alkyl group may, for example, be methyl, propyl, isopropyl, butyl, isobutyl, hexyl and, most preferably, ethyl.

In another embodiment of the invention, the agent is a monoester or polyester of a saturated or cis-unsaturated $C_{10}$-$C_{24}$ aliphatic acid, preferably $C_{16}$-$C_{20}$, most preferably $C_{18}$ fatty acid, with a polyol having at least four hydroxy groups such as, but not being limited to, erythritol, pentaerythritol, sorbitol or mannitol.

In a further embodiment of the invention, the agent is a monoester or polyester of a saturated or cis-unsaturated $C_{10}$-$C_{24}$ aliphatic acid, preferably $C_{16}$-$C_{20}$, most preferably $C_{18}$ fatty acid, with a monosaccharide such as glucose, mannose, fructose, galactose, or ribose, or with a disaccharide such as sucrose, lactose, maltose, or trehalose, or with a polysaccharide such as dextran, dextrine, or amylodextrin (soluble starch).

In still a further embodiment, the agent is an amide of a saturated or cis-unsaturated $C_{10}$-$C_{24}$ aliphatic acid, preferably $C_{16}$-$C_{20}$, most preferably $C_{18}$ fatty acid, with an aliphatic or aromatic amine such as methyl amine, ethyl amine, propyl amine, hexyl amine, aniline, benzyl amine, or with an amino acid such as glycine, alanine, leucine, lysine, tyrosine, or with a peptide, a protein or an aminosaccharide.

In a most preferred embodiment of the invention the ester is ethyl oleate (herein abbreviated as EOA) or mannide monooleate (herein abbreviated as MMO) or a combination of both.

The autoimmune and other immune-associated inflammatory disorders that can be treated according to the invention include, but are not limited to, organ-specific autoimmune diseases such as multiple sclerosis (MS), insulin-dependent diabetes mellitus (IDDM), rheumatoid arthritis, several forms of anemia (aplastic, hemolytic), autoimmune hepatitis, thyroiditis, iridocyclitis, scleritis, uveitis, orchitis, myasthenia gravis, idiopathic thrombocytopenia purpura, and inflammatory bowel diseases such as Crohn's disease and ulcerative colitis as well as systemic autoimmune diseases such as scleroderma and systemic sclerosis, Sjogren's syndrome, undifferentiated connective tissue syndrome, antiphospholipid syndrome, different forms of vasculitis (polyarteritis nodosa, allergic granulomatosis and angiitis, Wegner's granulomatosis, Kawasaki disease, hypersensitivity vasculitis, Henoch-Schoenlein purpura, Behcet's syndrome, Takayasu arteritis, giant cell arteritis, thromboangitis obliterans), systemic lupus erythematosus, polymyalgia rheumatica, psoriasis vulgaris and psoriatic arthritis, polymyositis and other idiopathic inflammatory myopathies, relapsing panniculitis, relapsing polychondritis, lymphomatoid granulomatosis, erythema nodosum, ankylosing spondylitis, Reiter's syndrome, and different forms of inflammatory dermatitis. The agents may further be used in the treatment of allergies and graft-versus-host disease and to prevent graft rejection.

The pharmaceutical compositions of the invention may comprise, besides the active ingredient, a pharmaceutically acceptable carrier and inert excipients. The agent can be administered by any suitable route such as, but not limited to, orally, topically, subcutaneously, and intramuscularly. These compositions can be made by conventional methods known to those skilled in the art, for example as described in "Remington's Pharmaceutical Science", A. R. Gennaro, ed., 17th edition, 1985, Mack Publishing Company, Easton, Pa., USA.

The invention will now be illustrated by the following non-limiting examples.

EXAMPLES

Materials and Methods
Mice. Female SJL/J (H-2$^s$) mice were purchased from Jackson Laboratories (Bar Harbor, Me., USA). All mice were 2-3 months old when used in the experiments.
Materials. The PLP 139-151 peptide consisting of amino acids 139-151 of the sequence of mouse PLP, which is encephalitogenic for SJL/J mice (Tuohy et al., 1994), was synthesized by the Weizmann Institute Synthesis Unit, using a solid-phase technique on a peptide synthesizer (Applied Biosystems Inc., Foster City, Calif., USA). EAE induced by PLP 139-151 peptide in SJL/J mice was used as a model for MS as well as for other organ-specific T-cell mediated autoimmune inflammatory diseases.

Incomplete Freund's adjuvant (IFA), complete Freund's adjuvant (CFA), and *Mycobacterium tuberculosis* H37Ra were obtained from Difco (MI, USA); ethyl oleic acid ester (ethyl oleate, EOA) from ICN (CA, USA); mannide mono-oleate (MMO) from Sigma (Israel); and paraffin oil from Sigma (Israel).
Induction of EAE. Mice were injected s.c. under general anesthesia at two sites in the flank with 100 μl of emulsion containing 200 μg PLP 139-151 in CFA containing 500 μg *Mycobacterium tuberculosis* (Difco, MI, USA). Alternatively, the mice were injected s.c. in the four paws with 200 μl (total volume) of emulsion containing mouse spinal cord homogenate (MSCH; 600 μg) and *Mycobacterium tuberculosis* (400 μg). Following the encephalitogenic challenge, mice were observed daily and clinical manifestations of EAE were scored on a scale of 0-5, wherein 0: no clinical signs, 1: flaccid tail, 2: hind limb paralysis, 3: hind limb paralysis and paresis of the fore limbs, 4: complete paralysis of the four limbs, 5: death.
Treatment of EAE by s.c. or i.p. administration of EOA, MMO or IFA. At indicated times, mice were injected s.c. in the flank or i.p. with 100 μl of EOA, MMO, or IFA in an oil form.

Example 1

Protection Against EAE by Subcutaneous Administration of EOA

The effect of EOA on the development of EAE was tested in SJL/J mice which develop severe clinical EAE upon immunization with PLP 139-151/CFA. From the day of the encephalitogenic challenge (day 0), until overt neurological impairment was first detected (loss of tail tonus, day 11-12 post-immunization), mice received daily s.c. injection of EOA (100 μl). Subsequently, EOA was administered (s.c.) every alternate day (day 13, 15 and 17), followed by three more injections of EOA on days 20, 23 and 26. As seen in FIG. 1, treatment with EOA resulted in significantly reduced clinical severity and incidence of EAE. As compared to the untreated control group where 5 out of 5 mice developed paralysis with maximal mean clinical score of 1.67±0.29, only 2 out of the 5 EOA-treated mice developed EAE, and with only mild clinical impairment (mean maximal severity=0.5±0.32, $\chi^2$=0.031 compared to control group). These results indicate that EOA might have a beneficial effect on the development of EAE.

Example 2

Protection Against EAE by Intraperitoneal Administration of EOA

Figure 2:
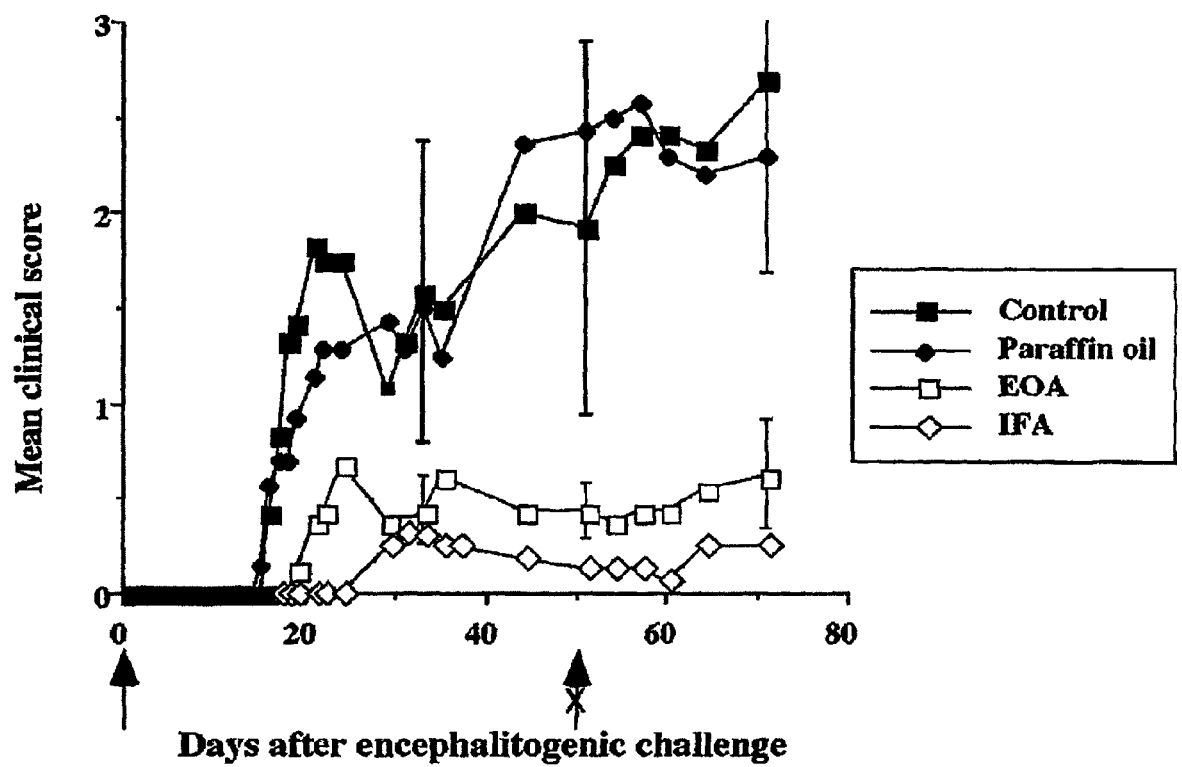
FIG. 2 shows that intraperitoneal (i.p.) administration of EOA protects against the development of EAE. Four groups of SJL/J mice (7-8 mice per group) were induced to develop EAE by PLP 139-151/CFA. Each group was injected daily i.p. with PBS (control), EOA, paraffin oil or IFA, from the day of encephalitogenic challenge (day 0). Treatment was stopped on day 50 and mice were followed and scored for disease progression until day 70.

The beneficial effect of EOA on EAE was further tested using a different route of administration, via i.p. injection. An additional group of paraffin oil-treated mice was included as an "oil control". EAE was induced in SJL/J mice with PLP 139-151/CFA. The EOA- or paraffin oil-treated mice were daily injected i.p. with 100 μl of the relevant oil, from the day of the encephalitogenic challenge (day 0). Treatment was stopped on day 50 and mice were followed and scored for disease progression until day 70. As shown in FIG. 2, treatment with paraffin oil had no effect on disease development and, similar to control untreated mice, 8 out of 8 mice developed severe clinical EAE with mean maximal clinical score of 2.70±1.02. In contrast, the 5 out of 8 EOA-treated mice, which developed EAE, the onset of which was delayed, presented with only very mild neurological impairment (maximal mean score 0.63±0.28, p=0.043 compared to control groups). As can be seen in FIG. 2, the protective effect of the EOA treatment was long lasting, as the mice remained stable for 20 days after cessation of EOA treatment. It is noteworthy that an identical treatment protocol with IFA, which contains another derivative of oleic acid, mannide mono-oleate (MMO), was as effective as EOA in protecting against EAE and preventing disease progression (FIG. 2).

Example 3

Protection Against EAE by Intraperitoneal Administration of MMO

Figure 3:
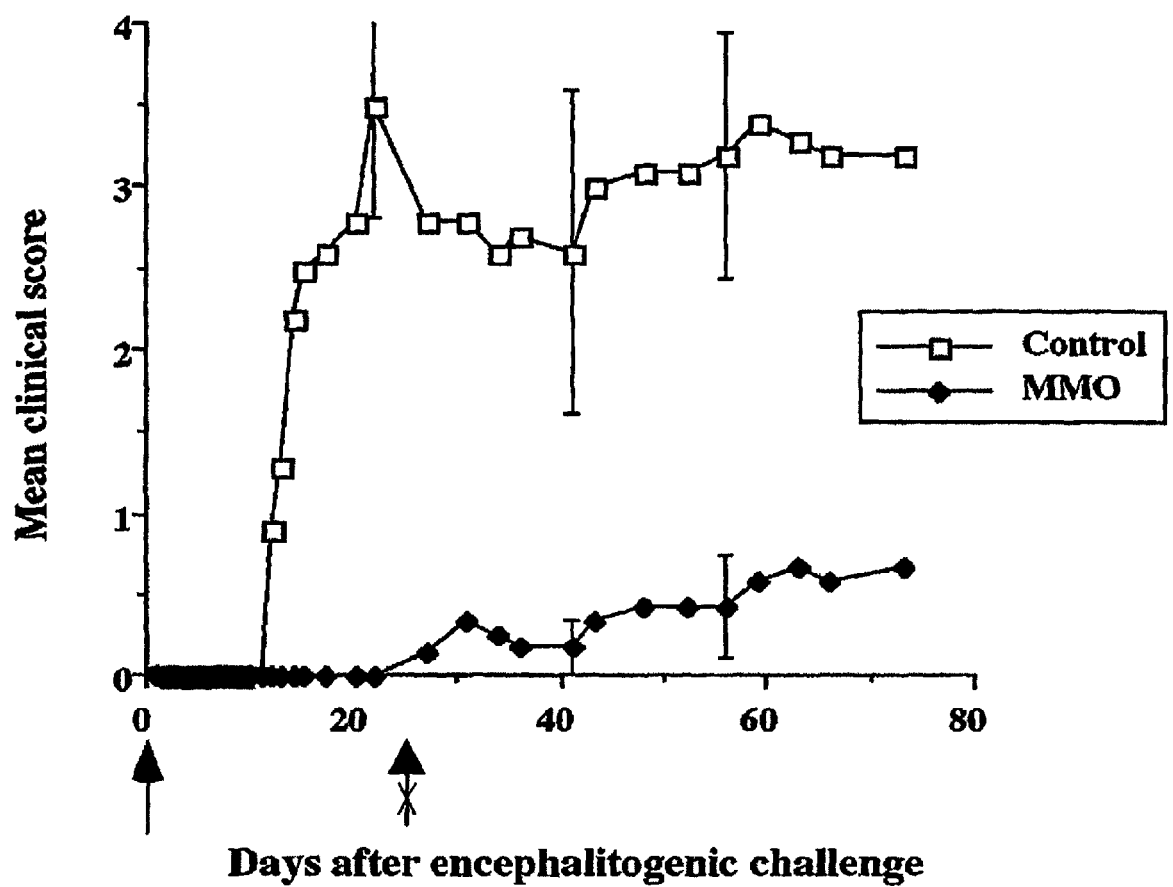
FIG. 3 shows that i.p. administration of mannide monooleate (MMO) protects against the development of EAE. SJL/J mice (5-6 mice per group) were induced to develop EAE with PLP 139-151/CFA. 100 μl of PBS (control) or MMO were daily-injected i.p. from the day of encephalitogenic challenge (day 0). Treatment was stopped on day 25 and the scoring of clinical signs was continued up to day 73 post-encephalitogenic challenge.

The possibility that the protective effect of IFA may be attributed to MMO was tested with daily administration of MMO from the day of the encephalitogenic challenge (day 0). Administration of MMO was stopped on day 25 post-immunization, and scoring of the clinical signs was continued up to day 73 post-encephalitogenic challenge. Results in FIG. 3 show that MMO administered daily i.p. from day 0 completely abrogated disease development. On day 20, when control mice (5 EAE-affected mice out of 5) had reached a mean maximal clinical score of 3.4±0.69, all 6 MMO-treated mice had remained free of any clinical sign of EAE (p=0.02). From day 25, when the daily i.p. administration of MMO was discontinued, very mild clinical signs appeared with time in 3 out of the 6 mice. On day 40 (15 days after MMO injections were stopped), the mean maximal clinical score in the MMO-treated group was 0.17±0.11, compared to the mean maximal clinical of 2.6±0.99 in the control group (p=0.014). On day 73 (48 days after MMO injections were stopped), the mean maximal clinical score in the MMO-treated mice was 0.67±0.44 as compared to 3.2±0.75 in the control group (p=0.012).

Example 4

Figure 4:
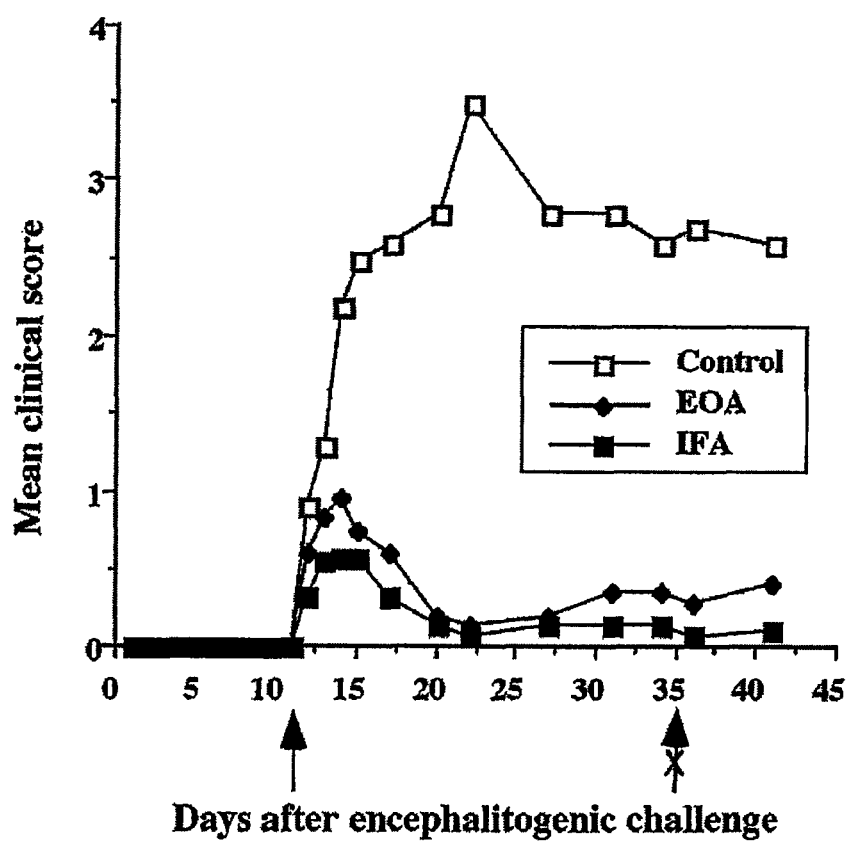
FIGS. 4A-4C show abrogation of disease progression and reversal of clinical signs of EAE by i.p. administration of EOA or IFA.
Figure 4:
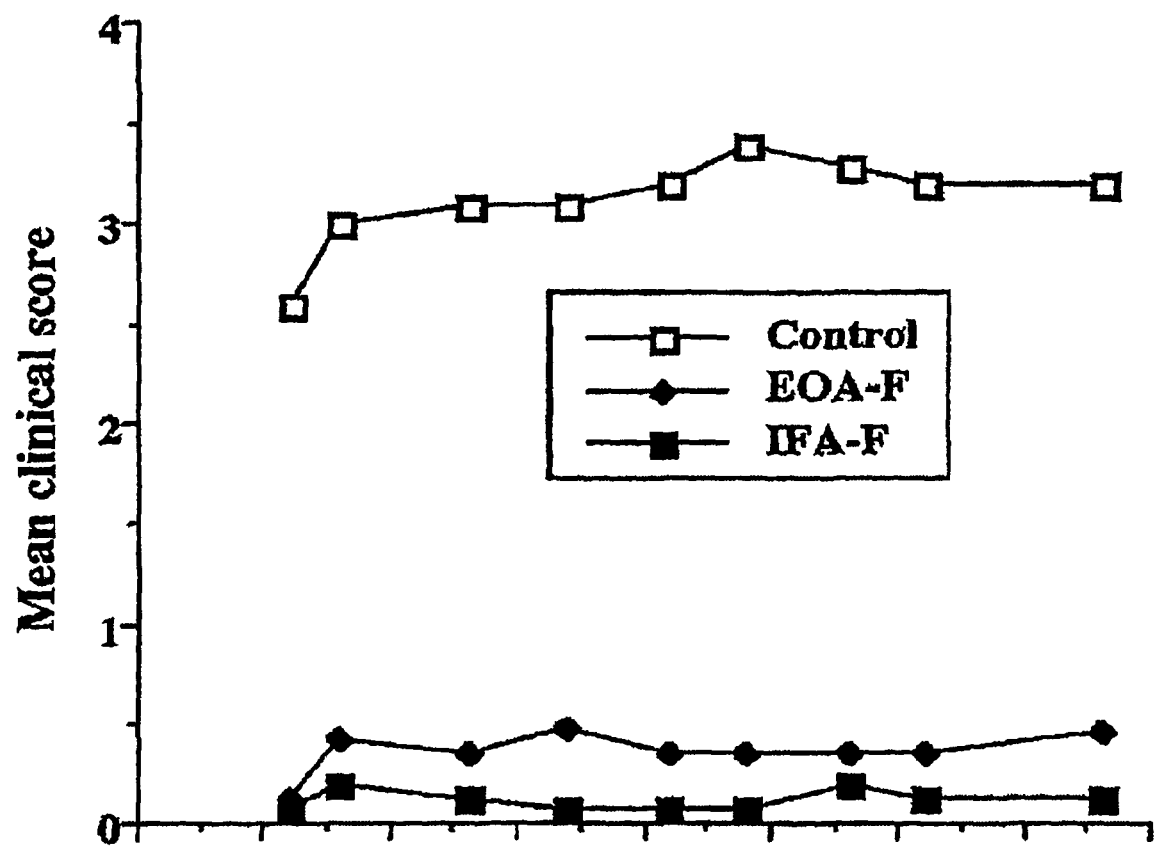
Figure 4:
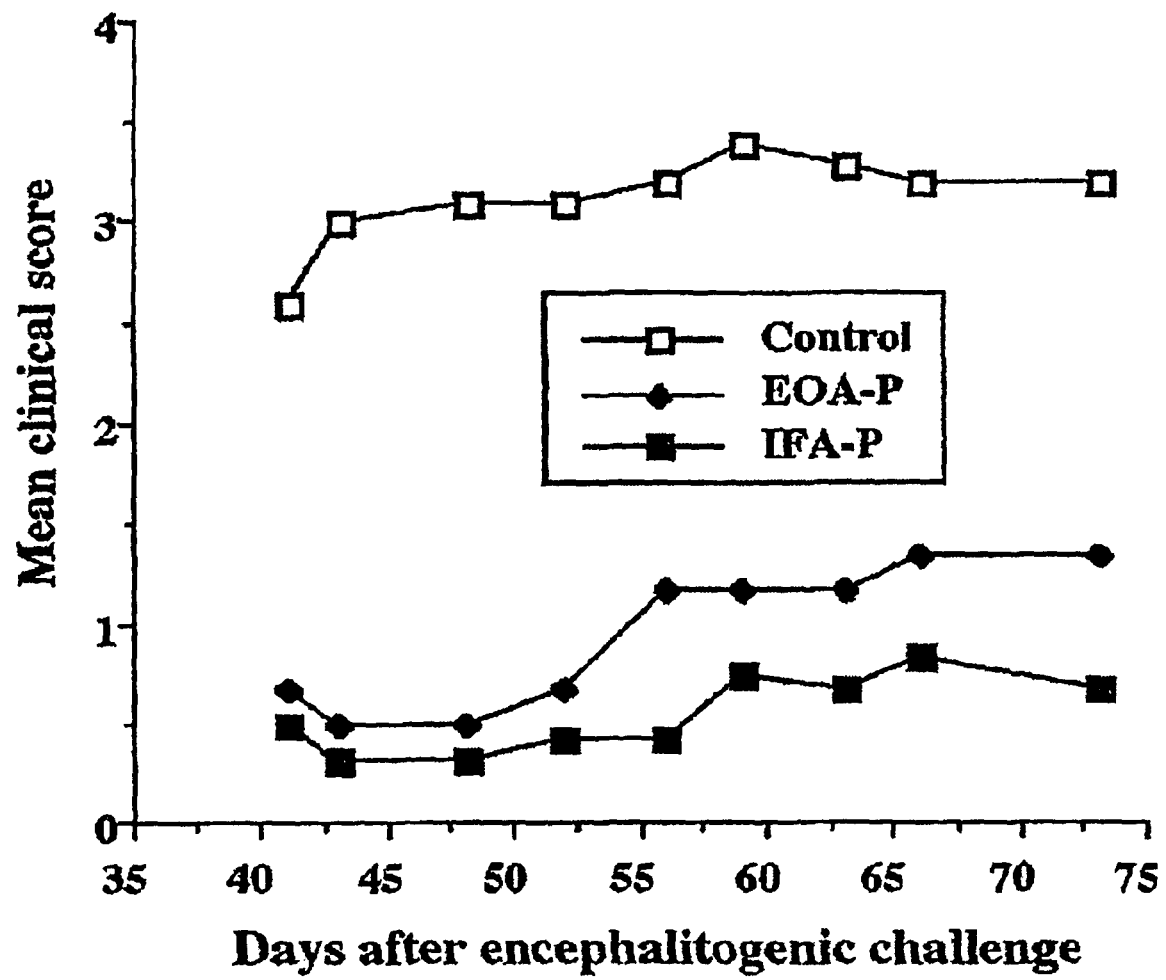

Abrogation of Disease Progression and Reversal of Clinical Signs of EAE by i.p. Administration of EOA In view of EOA strong protective effect against EAE, we further analyzed whether it could also treat an ongoing disease. The potential therapeutic effect of EOA was assessed on SJL/J mice immunized for induction of EAE with PLP 139-151/CFA. With our standard immunization protocol, the first overt clinical signs of EAE generally appear on day 11-12. Accordingly, treatment with EOA (daily i.p. injection with 100 μl EOA; 13 mice treated) was initiated on day 12 post-immunization when over 60% of the mice already showed clinical symptoms. As shown in FIG. 4A, i.p. administration of EOA beginning at the time of clinical onset of EAE, immediately arrested the worsening of the clinical symptoms of EAE, as compared to control mice. Furthermore, continuing treatment with EOA resulted not only in immediate abrogation of disease progression, but also in a complete reversal of the clinical symptoms within 8-10 days after treatment was initiated (day 20, FIG. 4A). Thus, while disease in control mice progressed to a mean maximal clinical score of 3.5±0.69, the progression of the disease in the EOA-treated mice was arrested at a maximal mean score of 0.83±0.53 immediately after the first injection of EOA, and the clinical symptoms decreased thereafter. As can be seen clearly in FIG. 4A, on days 20-21, when the symptoms in the control mice reached maximal clinical severity (mean score=3.5±0.69), the EOA-treated mice were almost free of clinical signs of EAE (mean maximal clinical score=0.17±0.11). Treatment with EOA was continued until day 35 post-immunization with no obvious reappearance of clinical symptoms of EAE (FIG. 4A). A similar regimen of treatment with IFA was followed (14 mice treated), and similar or better therapeutic effect on EAE was observed (FIG. 4A).

On day 40, after 9 days of withholding treatment with EOA or IFA, the mice had remained stable with no evidence of disease exacerbation or development of relapses (FIG. 4A). To further assess the efficacy of the treatments, each treatment group was subdivided on day 40 into two subgroups, according to the degree of recovery from disease. Thus, for each treatment group (EOA or IFA), mice that had recovered with full reversal of clinical signs of EAE, were pooled in one subgroup, while the other subgroup comprised mice with residual clinical signs of EAE (weak to flaccid tail). These subgroups are hereafter referred to as EOA-F or IFA-F (fully recovered subgroups; 8 and 11 mice in the EOA-F and IFA-F subgroups, respectively) and EOA-P or IFA-P (partially recovered subgroups; 5 and 3 mice in the EOA-P and IFA-P subgroups, respectively). In the EOA-F and IFA-F subgroups, which were free of clinical signs of EAE, the mice remained withheld of treatment and were monitored for clinical expression of EAE (FIG. 4B). On the other hand, daily i.p. treatment with EOA or IFA was reinstated for another 40 days in the mice of the EOA-P and IFA-P subgroups, respectively (FIG. 4C). Results obtained demonstrate that the reversal of the clinical signs of EAE following treatment with EOA or IFA is stable and that the relative recovery is long lasting. Hence, the mice that had completely recovered (EOA-F or IFA-F) and were not further treated, remained healthy or developed only very mild clinical signs of EAE (mean maximal clinical score<0.5) (FIG. 4B). In mice which had not fully recovered during the first course of treatment (EOA-P or IFA-P), the second course of daily i.p. administration of EOA or IFA, respectively, had no further ameliorating effect on the clinical signs of EAE (FIG. 4C); the mice remained relatively stable with mild clinical signs (mean maximal clinical score for EOA-P=1.3±0.19, for IFA-P=0.68±0.20), which were nevertheless significantly lower than those observed in untreated control mice (mean maximal clinical score=3.1±0.7).

Example 5

Abrogation of Disease Progression by s.c. Administration of EOA and MMO

Figure 5:
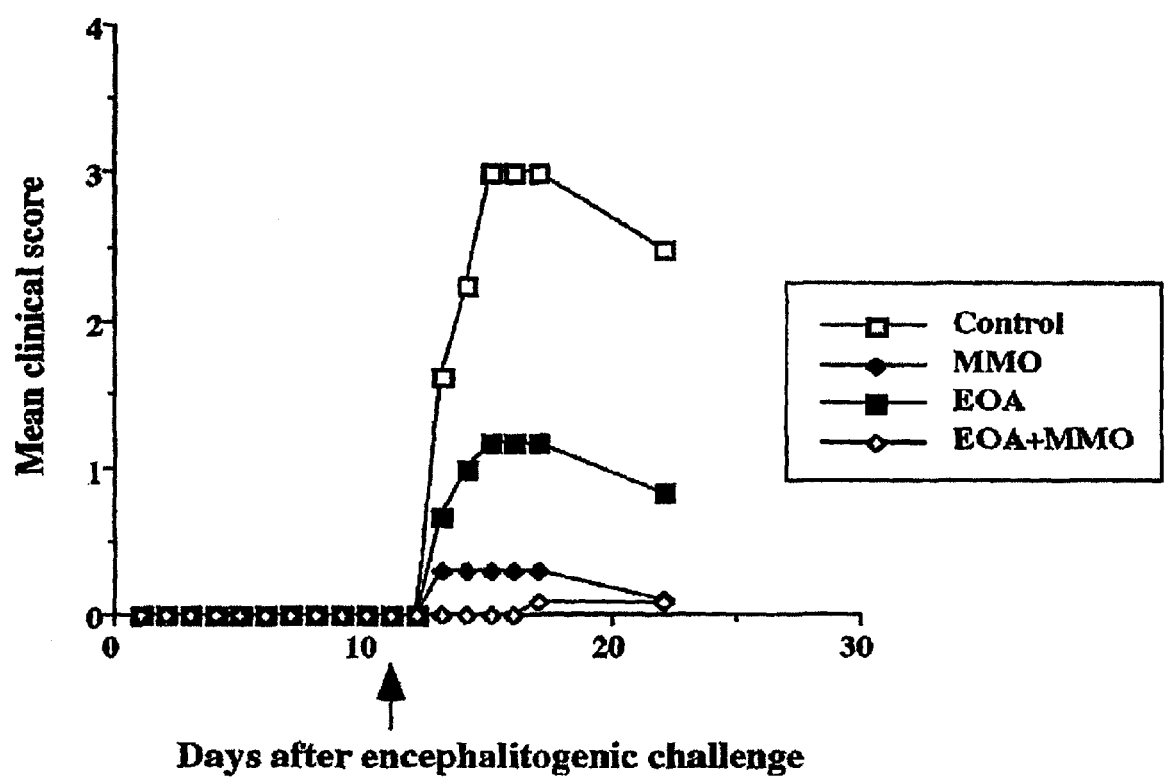
FIG. 5 shows abrogation of disease (EAE) progression by s.c. administration of EOA and MMO. SJL/J mice were induced to develop EAE by PLP 139-151/CFA. The mice (5-6 mice per group) were daily-injected s.c. with 100 μl of PBS (control), MMO, EOA, or a 1:1 mixture of EOA+MMO, starting from day 11 post-encephalitogenic challenge, just prior to the clinical onset of EAE.

The potential therapeutic effect of EOA and MMO was further assessed with daily s.c. administration of each or of a 1:1 combination thereof, starting from day 11 post-encephalitogenic challenge, just prior to the clinical onset of EAE. As shown in FIG. 5, all treatments were highly effective in arresting disease progression, with the 1:1 mixture of MMO and EOA being most potent. Thus, on day 22, when the experiment was stopped, the mean clinical score of the PBS-treated control mice was 2.5±0.84, while the mean clinical score of the EOA-treated mice was 0.83±0.40 (p=0.07), and that of the MMO- and MMO+EOA-treated mice was 0.08±0.08 (p=0.03) (FIG. 5).

Figure 6:
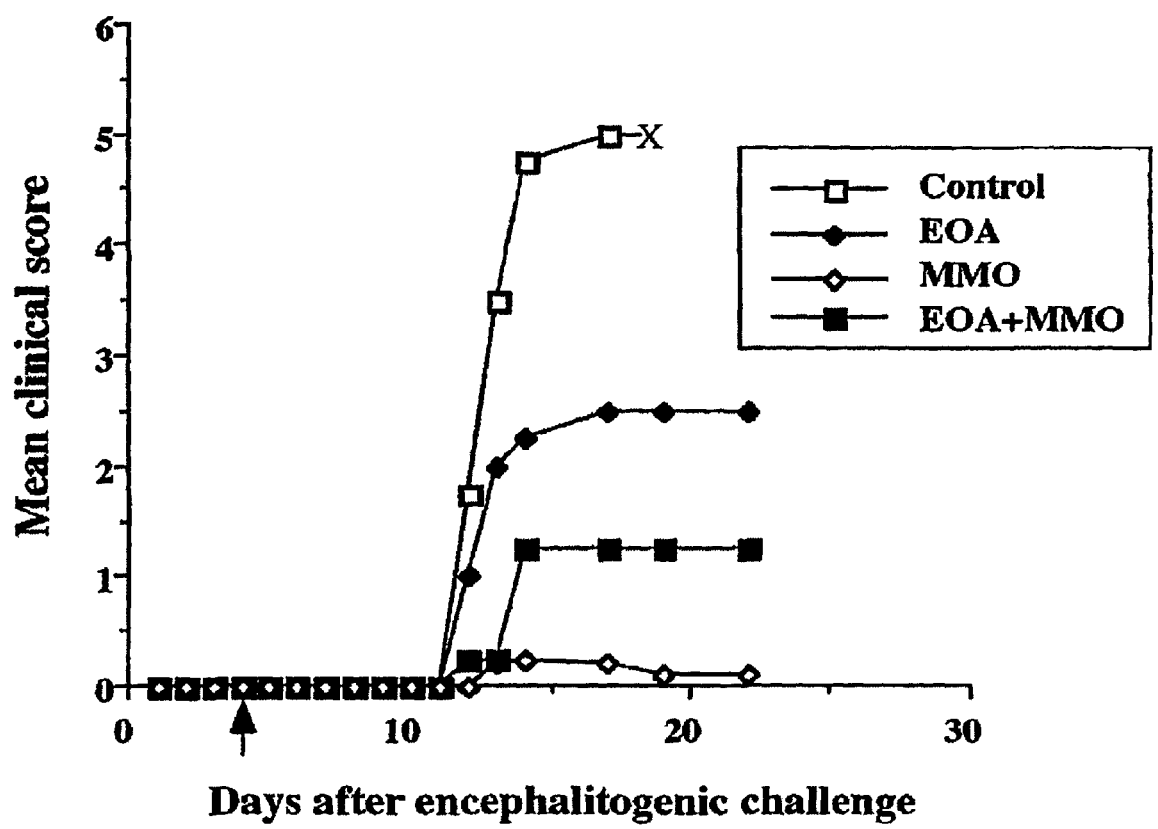
FIG. 6 shows that s.c. administration of EOA or MMO protects against the development of EAE induced by mouse spinal cord homogenate (MSCH). SJL/J mice were induced to develop EAE by injecting MSCH emulsified in CFA. Mice of each group (4 mice per group) were injected daily s.c. with 100 μl of PBS (control) or with EOA, MMO or a 1:1 mixture of EOA+MMO, starting from day 4 post-encephalitogenic challenge. X indicates death of all mice in the group.

Protection by s.c. administration of EOA or MMO or a mixture of EOA+MMO was effective not only for EAE induced by a peptide representing a single encephalitogenic epitope (PLP 139-151, FIG. 5), but also for EAE induced with mouse spinal cord homogenate (MSCH), which includes all possible encephalitogenic proteins. As shown in FIG. 6, following encephalitogenic challenge with MSCH/CFA, all control mice had died by day 15 post-immunization; in contrast, mice treated daily by s.c. administration of EOA or MMO or a mixture of EOA+MMO from day 4 after the encephalitogenic challenge, presented markedly reduced clinical severity, with MMO treatment resulting in almost complete abrogation of disease development.

Example 6

Treatment of Other Autoimmune Diseases

Although the mechanisms by which EOA, MMO or a mixture of EOA+MMO effectively suppress the development of PLP 139-151- or MSCH-induced EAE and abrogate disease progression in mice are not yet understood, the mode of action by which EOA and MMO block the development of EAE is obviously not by targeting the encephalitogenic T-cells via an antigen-specific mechanism. These results indicate that treatment by EOA, MMO or a mixture of EOA+MMO is effective also in blocking the development of other autoimmune diseases.

6.1 Treatment of Rheumatoid Arthritis

Collagen-induced autoimmune arthritis in laboratory animals resembles human rheumatoid arthritis in several aspects, and is widely used as a model for the human counterpart (Harris, 1989). The disease can be induced by injecting H-$2^q$ or H-$2^r$ mice with collagen type II dissolved in 0.01M acetic acid and emulsified at 1:1 ratio with CFA (Stuart et al., 1982). Arthritis, evidenced by marked swelling and erythema of the fore and hind paws, develop from 20-25 days post-immunization (Wooley et al., 1981). On the basis of effective modulation of EAE by EOA or MMO, it is expected that daily injections (s.c. or i.p.) of EOA or MMO or a mixture of EOA+MMO starting from 7-10 days before onset of the disease would protect the mice from developing arthritis. Furthermore, daily administration of EOA, MMO or a mixture of EOA+MMO is expected to abrogate disease progression, if applied from the time when clinical signs of arthritis can first be detected.

6.2 Treatment of Insulin-Dependent Diabetes Mellitus (IDDM)

IDDM is an autoimmune disease that results from the destruction of insulin-producing β cells in the pancreas islets of Langerhans. This destruction is manifested by mononuclear cell infiltrates and a chronic inflammatory process in the islets of affected individuals (Castano and Eisenbarth, 1990). IDDM develops spontaneously in NOD mice, providing an animal model system which highly resembles the human IDDM (Castano and Eisenbarth, 1990). NOD mice spontaneously develop insulitis at the age of 4-6 weeks and hyperglycemia from 12 weeks of age (Bach, 1994). In view of the results obtained with EAE, it is expected that daily injections (s.c. or i.p.) of EOA or MMO or a mixture of EOA+MMO starting at 3 weeks of age, would suppress the development of insulitis and of subsequent diabetes in the treated NOD mice. Furthermore, daily injections of EOA, MMO or EOA+MMO at 10-11 weeks of age is expected to abrogate progression into full-blown diabetes.

6.3 Treatment of Other Autoimmune Diseases and Immune-Mediated Inflammation

The development of antibody-mediated autoimmune diseases such as lupus erythematosus or myasthenia gravis, is dependent on effective helper T-cells. It is therefore reasonable to assume that administration of EOA, MMO or a mixture of EOA+MMO could modulate the production of pathogenic antibodies via mechanism(s) which affect the T-helper cells. Hence, EOA or MMO or a mixture of EOA+MMO, which are unlikely to be toxic for humans, can be considered as potential agents for the treatment of a variety of autoimmune diseases as well as for graft-versus-host disease and graft rejection, which are associated with inflammatory reactions mediated by T-cells.

REFERENCES

Bach, J.-F. 1994. Insulin-dependent diabetes mellitus as an autoimmune disease. *Endoc. Rev.* 15: 516-542.

Castano, L., and Eisenbarth, G. S. 1990. Type I diabetes: a chronic autoimmune disease of human, mouse and rat. *Annu. Rev. Immunol.* 8: 647-680.

Harris, E. D. 1989. Pathogenesis of rheumatoid arthritis. In "*Textbook of Rheumatology*", $3^{rd}$ Ed. (W. N. Kelley, D. H. Harris, S. Ruddy and C. B. Sledge, eds.) W. B. Saunders, Philadelphia, p. 905.

Kerlero de Rosbo, N., and A. Ben-Nun. 1998. T-cell responses to myelin antigens in multiple sclerosis: Relevance of the predominant autoimmune reactivity to myelin oligodendrocyte glycoprotein. *J. Autoimmun.* 11: 287-299.

Kerlero de Rosbo, N. and Ben-Nun, A. 1999. Experimental autoimmune encephalomyelitis induced by various antigens of the central nervous system. Overview and relevance to multiple sclerosis. In "*The Decade of Autoimmunity 1987-1997*" (Y. Shoenfeld, ed.), Elsevier Science, Amsterdam, pp. 169-177.

Stuart, J. M., Townes, A. S., and Kang, A. H. 1982. Nature and specificity of the immune response to collagen in type II collagen-induced arthritis in mice. *J. Clin. Invest.* 69: 673.

Tuohy, V. K. 1994. Peptide determinants of myelin proteolipid protein (PLP) in autoimmune disease: A review. *Neurochem. Res.* 19: 935-944.

Wooley, P. H., Luthra, H. W., Stuart, J. M. and David, C. S. 1981. Type II collagen-induced arthritis in mice. I. Major histocompatibility complex (I region) linkage and antibody correlates. *J. Exp. Med.* 154: 688.

The invention claimed is:

1. A method for the treatment of a patient having multiple sclerosis, comprising
    administering to said patient a therapeutically effective amount of an agent selected from the group consisting of ethyl oleate, mannide monooleate, and a combination thereof.

2. A method according to claim 1 wherein said agent is ethyl oleate.

3. A method according to claim 1 wherein said agent is mannide monooleate.

4. A method according to claim 1 wherein said agent is a combination of ethyl oleate and mannide monooleate.

5. A method according to claim 4 wherein said agent is a 1:1 mixture of ethyl oleate and mannide monooleate.

6. A method according to claim 2, wherein said ethyl oleate is administered orally.

* * * * *